(12) United States Patent
Stem et al.

(10) Patent No.: US 10,279,171 B2
(45) Date of Patent: May 7, 2019

(54) METHODS OF SHIELDING IMPLANTABLE MEDICAL LEADS AND IMPLANTABLE MEDICAL LEAD EXTENSIONS

(71) Applicant: MEDTRONIC, INC., Minneapolis, MN (US)

(72) Inventors: Bryan D. Stem, Minneapolis, MN (US); James M. Olsen, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/804,020

(22) Filed: Jul. 20, 2015

(65) Prior Publication Data

US 2016/0022983 A1    Jan. 28, 2016

Related U.S. Application Data

(60) Provisional application No. 62/028,120, filed on Jul. 23, 2014.

(51) Int. Cl.
  *A61N 1/08* (2006.01)
  *A61N 1/05* (2006.01)
  *H01R 43/20* (2006.01)
(52) U.S. Cl.
  CPC ............. *A61N 1/08* (2013.01); *A61N 1/05* (2013.01); *H01R 43/20* (2013.01); *A61N 1/086* (2017.08)
(58) Field of Classification Search
  CPC ........ A61N 1/08; A61N 1/05; A61N 201/086; H01R 43/20

USPC .......................................................... 607/116
See application file for complete search history.

(56) References Cited

U.S. PATENT DOCUMENTS

| 2,433,480 A | 12/1947 | Rendich |
| 2,487,038 A | 11/1949 | Jasper |
| 3,788,329 A | 1/1974 | Friedman |
| 3,842,485 A | 10/1974 | Bemert |

(Continued)

FOREIGN PATENT DOCUMENTS

| EP | 0617978 | 10/1994 |
| EP | 0624383 | 11/1994 |

(Continued)

OTHER PUBLICATIONS

PCT Application No. PCT/US2015/0471171 International Search Report and Written Opinion dated Oct. 1, 2015.

(Continued)

*Primary Examiner* — Michael Carey
(74) *Attorney, Agent, or Firm* — Withers & Keys, LLC

(57) ABSTRACT

A shield layer is added to an existing lead or lead extension by applying the shield layer to the lead body between the proximal contact and distal electrode of the lead body. The shield layer may be covered with an outer insulative layer. An inner insulative layer may be applied over the lead body prior to adding the shield layer and the outer insulative layer. The shield layer may have a terminator applied to the end of the shield layer to prevent migration of the shield layer through the outer insulative layer. The shield layer may be of various forms including a tubular braided wire structure or a tubular foil. The tubular braided wire structure may be applied to the lead body by utilizing the lead body as a mandrel within a braiding machine.

16 Claims, 9 Drawing Sheets

(56) References Cited

U.S. PATENT DOCUMENTS

| | | |
|---|---|---|
| 3,915,174 A | 10/1975 | Preston |
| 4,033,355 A | 7/1977 | Amundson |
| 4,038,990 A | 8/1977 | Thompson |
| 4,214,804 A | 7/1980 | Little |
| 4,220,813 A | 9/1980 | Kyle |
| 4,280,507 A | 7/1981 | Rosenberg |
| 4,320,763 A | 3/1982 | Money |
| 4,350,169 A | 9/1982 | Dutcher |
| 4,383,225 A | 5/1983 | Mayer |
| 4,403,824 A | 9/1983 | Scott |
| 4,441,498 A | 4/1984 | Nordling |
| 4,628,942 A | 12/1986 | Sweeney et al. |
| 4,683,895 A | 8/1987 | Pohndorf |
| 4,711,027 A | 12/1987 | Harris |
| 4,726,379 A | 2/1988 | Altman et al. |
| 4,852,585 A | 8/1989 | Heath |
| 4,906,241 A | 3/1990 | Noddin |
| 4,920,980 A | 5/1990 | Jackowski |
| 4,922,607 A | 5/1990 | Doan et al. |
| 4,934,380 A | 6/1990 | De Toledo |
| 4,947,866 A | 8/1990 | Lessar et al. |
| 4,951,672 A | 8/1990 | Buchwald et al. |
| 4,991,583 A | 2/1991 | Silvian |
| 5,003,992 A | 4/1991 | Holleman |
| 5,005,587 A | 4/1991 | Scott |
| 5,012,045 A | 4/1991 | Sato |
| 5,018,523 A | 5/1991 | Bach, Jr. et al. |
| 5,020,544 A | 6/1991 | Dahl et al. |
| 5,020,545 A | 6/1991 | Soukup |
| 5,036,862 A | 8/1991 | Pohndorf |
| 5,040,544 A | 8/1991 | Lessar et al. |
| 5,063,932 A | 11/1991 | Dahl et al. |
| 5,197,468 A | 3/1993 | Proctor et al. |
| 5,213,111 A | 5/1993 | Cook et al. |
| 5,217,010 A | 6/1993 | Tsitlik et al. |
| 5,231,078 A | 7/1993 | Riebman et al. |
| 5,243,996 A | 9/1993 | Hall |
| 5,246,438 A | 9/1993 | Langberg |
| 5,260,128 A | 11/1993 | Ishii et al. |
| 5,265,608 A | 11/1993 | Lee et al. |
| 5,265,623 A | 11/1993 | Kroll et al. |
| 5,271,417 A | 12/1993 | Swanson et al. |
| 5,308,664 A | 5/1994 | House et al. |
| 5,314,459 A | 5/1994 | Swanson et al. |
| 5,323,776 A | 6/1994 | Blakely et al. |
| 5,335,657 A | 8/1994 | Terry, Jr. et al. |
| 5,349,133 A | 9/1994 | Rogers |
| 5,360,441 A | 11/1994 | Otten |
| 5,366,496 A | 11/1994 | Dahl et al. |
| 5,370,644 A | 12/1994 | Langberg |
| 5,374,286 A | 12/1994 | Morris |
| 5,374,778 A | 12/1994 | Hashimoto et al. |
| 5,417,719 A | 5/1995 | Hull et al. |
| 5,456,705 A | 10/1995 | Morris |
| 5,458,629 A | 10/1995 | Baudino et al. |
| 5,458,631 A | 10/1995 | Xavier |
| 5,466,252 A | 11/1995 | Soukup et al. |
| 5,473,812 A | 12/1995 | Morris et al. |
| 5,476,496 A | 12/1995 | Strandberg et al. |
| 5,485,667 A | 1/1996 | Kleshinski |
| 5,500,013 A | 3/1996 | Buscemi et al. |
| 5,504,274 A | 4/1996 | McCabe et al. |
| 5,514,172 A | 5/1996 | Mueller |
| 5,515,848 A | 5/1996 | Corbett, III et al. |
| 5,523,534 A | 6/1996 | Meister et al. |
| 5,523,578 A | 6/1996 | Herskovic |
| 5,527,348 A | 6/1996 | Winkler |
| 5,534,018 A | 7/1996 | Wahlstrand |
| 5,552,565 A | 9/1996 | Cartier et al. |
| 5,571,157 A | 11/1996 | McConnell |
| 5,572,594 A | 11/1996 | DeVoe et al. |
| 5,591,218 A | 1/1997 | Jacobson |
| 5,594,304 A | 1/1997 | Graber |
| 5,606,981 A | 3/1997 | Tartacower et al. |
| 5,609,622 A | 3/1997 | Soukup et al. |
| 5,628,780 A | 5/1997 | Helland et al. |
| 5,629,622 A | 5/1997 | Scampini |
| 5,643,254 A | 7/1997 | Scheldrup et al. |
| 5,649,965 A | 7/1997 | Pons et al. |
| 5,662,697 A | 9/1997 | Li et al. |
| 5,676,659 A | 10/1997 | McGurk |
| 5,676,694 A | 10/1997 | Boser et al. |
| 5,683,435 A | 11/1997 | Truex et al. |
| 5,683,444 A | 11/1997 | Huntley et al. |
| 5,697,909 A | 12/1997 | Eggers et al. |
| 5,697,958 A | 12/1997 | Paul et al. |
| 5,702,437 A | 12/1997 | Baudino |
| 5,706,826 A | 1/1998 | Schwager |
| 5,722,998 A | 3/1998 | Prutchi et al. |
| 5,727,552 A | 3/1998 | Ryan |
| 5,751,539 A | 5/1998 | Stevenson et al. |
| 5,766,232 A | 6/1998 | Grevious et al. |
| 5,782,241 A | 7/1998 | Felblinger et al. |
| 5,795,341 A | 8/1998 | Samson |
| 5,807,258 A | 9/1998 | Cimochowski et al. |
| 5,814,076 A | 9/1998 | Brownlee |
| 5,827,997 A | 10/1998 | Chung et al. |
| 5,830,136 A | 11/1998 | Delonzor et al. |
| 5,842,966 A | 12/1998 | Markoll |
| 5,842,986 A | 12/1998 | Avrin et al. |
| 5,851,226 A | 12/1998 | Skubitz et al. |
| 5,897,584 A | 4/1999 | Herman |
| 5,905,627 A | 5/1999 | Brendel et al. |
| 5,927,345 A | 7/1999 | Samson |
| 5,931,861 A | 8/1999 | Werner et al. |
| 5,954,760 A | 9/1999 | Jarl |
| 5,964,705 A | 10/1999 | Truwit et al. |
| 5,968,087 A | 10/1999 | Hess |
| 5,970,429 A | 10/1999 | Martin |
| 5,942,966 A | 12/1999 | Markoll |
| 6,004,269 A | 12/1999 | Crowley |
| 6,016,447 A | 1/2000 | Juran et al. |
| 6,024,703 A | 2/2000 | Zanelli et al. |
| 6,032,063 A | 2/2000 | Hoar et al. |
| 6,033,408 A | 3/2000 | Gage et al. |
| 6,055,457 A | 4/2000 | Bonner |
| 6,101,417 A | 8/2000 | Vogel et al. |
| 6,103,037 A | 8/2000 | Wilson |
| 6,108,582 A | 8/2000 | Fischer, Sr. |
| 6,132,390 A | 10/2000 | Cookston et al. |
| 6,141,593 A | 10/2000 | Patag |
| 6,143,013 A | 11/2000 | Samson et al. |
| 6,152,746 A | 11/2000 | Brown |
| 6,156,029 A | 12/2000 | Mueller |
| 6,195,267 B1 | 2/2001 | MacDonald et al. |
| 6,198,807 B1 | 3/2001 | DeSena |
| 6,198,972 B1 | 3/2001 | Hartlaub et al. |
| 6,209,764 B1 | 4/2001 | Hartlaub et al. |
| 6,240,322 B1 | 5/2001 | Peterfeso |
| 6,258,071 B1 | 7/2001 | Brookes |
| 6,265,466 B1 | 7/2001 | Glatkowski |
| 6,269,148 B1 | 7/2001 | Jessop et al. |
| 6,284,971 B1 | 9/2001 | Atalar et al. |
| 6,302,740 B1 | 10/2001 | Holmstrom |
| 6,348,070 B1 | 2/2002 | Teissl et al. |
| 6,424,234 B1 | 7/2002 | Stevenson |
| 6,471,699 B1 | 10/2002 | Fleischman et al. |
| 6,488,704 B1 | 12/2002 | Connelly et al. |
| 6,494,916 B1 | 12/2002 | Babalola et al. |
| 6,501,991 B1 | 12/2002 | Honeck et al. |
| 6,503,648 B1 | 1/2003 | Wang |
| 6,506,972 B1 | 1/2003 | Wang |
| 6,529,774 B1 | 3/2003 | Greene |
| 6,538,191 B1 | 3/2003 | MacDonald |
| 6,583,361 B2 | 6/2003 | Clouet |
| 6,606,521 B2 | 8/2003 | Paspa et al. |
| 6,640,137 B2 | 10/2003 | MacDonald |
| 6,648,690 B2 | 11/2003 | Saito et al. |
| 6,660,116 B2 | 12/2003 | Wolf et al. |
| 6,671,544 B2 | 12/2003 | Baudino |
| 6,671,554 B2 | 12/2003 | Gibson et al. |
| 6,673,999 B1 | 1/2004 | Wang et al. |
| 6,675,033 B1 | 1/2004 | Lardo et al. |
| 6,689,835 B2 | 2/2004 | Amarasekera et al. |

(56) References Cited

U.S. PATENT DOCUMENTS

| | | |
|---|---|---|
| 6,695,761 B2 | 2/2004 | Oschman et al. |
| 6,708,051 B1 | 3/2004 | Durousseau |
| 6,711,440 B2 | 3/2004 | Deal et al. |
| 6,712,844 B2 | 3/2004 | Pacetti et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,735,471 B2 | 5/2004 | Hill et al. |
| 6,741,892 B1 | 5/2004 | Meadows et al. |
| 6,743,055 B1 | 6/2004 | Flynn |
| 6,750,055 B1 | 6/2004 | Connelly et al. |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,768,053 B1 | 7/2004 | Wang et al. |
| 6,778,856 B2 | 8/2004 | Connelly et al. |
| 6,792,316 B2 | 9/2004 | Sass |
| 6,793,642 B2 | 9/2004 | Connelly et al. |
| 6,795,730 B2 | 9/2004 | Connelly et al. |
| 6,795,736 B2 | 9/2004 | Connelly et al. |
| 6,799,067 B2 | 9/2004 | Pacetti |
| 6,799,069 B2 | 9/2004 | Weiner et al. |
| 6,815,609 B1 | 11/2004 | Wang et al. |
| 6,819,954 B2 | 11/2004 | Connelly |
| 6,819,958 B2 | 11/2004 | Weiner et al. |
| 6,844,492 B1 | 1/2005 | Wang et al. |
| 6,845,259 B2 | 1/2005 | Pacetti et al. |
| 6,845,267 B2 | 1/2005 | Harrison et al. |
| 6,846,985 B2 | 1/2005 | Wang et al. |
| 6,850,805 B2 | 2/2005 | Connelly et al. |
| 6,852,091 B2 | 2/2005 | Edwards et al. |
| 6,863,653 B1 | 3/2005 | Zanelli et al. |
| 6,864,418 B2 | 3/2005 | Wang et al. |
| 6,869,683 B2 | 3/2005 | Sakurai et al. |
| 6,871,091 B2 | 3/2005 | Wilkinson et al. |
| 6,872,882 B2 | 3/2005 | Fritz |
| 6,875,180 B2 | 4/2005 | Weiner et al. |
| 6,879,861 B2 | 4/2005 | Benz et al. |
| 6,882,519 B2 | 4/2005 | Uzawa et al. |
| 6,895,280 B2 | 5/2005 | Meadows et al. |
| 6,901,287 B2 | 5/2005 | Davis et al. |
| 6,901,290 B2 | 5/2005 | Foster et al. |
| 6,906,256 B1 | 6/2005 | Wang |
| 6,920,361 B2 | 7/2005 | Williams |
| 6,922,590 B1 | 7/2005 | Whitehurst |
| 6,925,328 B2 | 8/2005 | Foster et al. |
| 6,930,242 B1 | 8/2005 | Helfer |
| 6,937,906 B2 | 8/2005 | Terry et al. |
| 6,944,489 B2 | 9/2005 | Zeiljemaker et al. |
| 6,949,929 B2 | 9/2005 | Gray et al. |
| 6,954,674 B2 | 10/2005 | Connelly |
| 6,968,235 B2 | 11/2005 | Belden et al. |
| 6,968,236 B2 | 11/2005 | Hagele |
| 6,971,391 B1 | 12/2005 | Wang et al. |
| 6,980,865 B1 | 12/2005 | Wang et al. |
| 6,982,378 B2 | 1/2006 | Dickson |
| 6,985,775 B2 | 1/2006 | Reinke et al. |
| 6,993,387 B2 | 1/2006 | Connelly et al. |
| 6,999,818 B2 | 2/2006 | Stevenson et al. |
| 6,999,821 B2 | 2/2006 | Jenney et al. |
| 7,001,369 B2 | 2/2006 | Griffin et al. |
| 7,013,174 B2 | 3/2006 | Connelly et al. |
| 7,013,180 B2 | 3/2006 | Villaseca et al. |
| 7,015,392 B1 | 3/2006 | Dickenson |
| 7,015,393 B2 | 3/2006 | Weiner |
| 7,047,084 B2 | 5/2006 | Erickson |
| 7,050,855 B2 | 5/2006 | Zeijlemaker et al. |
| 7,058,192 B2 | 6/2006 | Muller et al. |
| 7,076,283 B2 | 7/2006 | Cho et al. |
| 7,076,302 B2 | 7/2006 | Scheiner |
| 7,082,328 B2 | 7/2006 | Funke |
| 7,082,337 B2 | 7/2006 | Sommer et al. |
| 7,103,413 B2 | 9/2006 | Swanson |
| 7,113,827 B2 | 9/2006 | Silvestri |
| 7,115,134 B2 | 10/2006 | Chambers |
| 7,118,693 B2 | 10/2006 | Glatkowski et al. |
| 7,123,013 B2 | 10/2006 | Gray |
| 7,125,409 B2 | 10/2006 | Truckai et al. |
| 7,162,302 B2 | 1/2007 | Wang et al. |
| 7,174,219 B2 | 2/2007 | Wahlstrand et al. |
| 7,187,980 B2 | 3/2007 | Osypka et al. |
| 7,233,825 B2 | 6/2007 | Jorgenson et al. |
| 7,257,449 B2 | 8/2007 | Bodner |
| 7,282,260 B2 | 10/2007 | LeGrande et al. |
| 7,286,871 B2 | 10/2007 | Cohen |
| 7,286,882 B2 | 10/2007 | Cole |
| 7,292,894 B2 | 11/2007 | Belden |
| 7,294,785 B2 | 11/2007 | Uutela et al. |
| 7,319,901 B2 | 1/2008 | Dublin |
| 7,363,090 B2 | 4/2008 | Halperin |
| 7,389,148 B1 | 6/2008 | Morgan |
| 7,540,865 B2 | 6/2009 | Griffin et al. |
| 7,548,788 B2 | 6/2009 | Chinn et al. |
| 7,591,831 B2 | 9/2009 | Parsonage et al. |
| 7,674,972 B2 | 3/2010 | Gladd et al. |
| 7,711,436 B2 | 5/2010 | Stone |
| 7,729,777 B2 | 6/2010 | Gray et al. |
| 7,738,942 B2 | 6/2010 | Weiner |
| 7,813,811 B2 | 10/2010 | Wingeier et al. |
| 7,819,826 B2 | 10/2010 | Diederich et al. |
| 7,822,484 B1 | 10/2010 | Zhao et al. |
| 7,828,833 B2 | 11/2010 | Haverkost |
| 7,844,343 B2 | 11/2010 | Wahlstrand |
| 7,844,344 B2 | 11/2010 | Wahlstrand |
| 7,853,332 B2 | 12/2010 | Olsen |
| 7,877,150 B2 | 1/2011 | Hoegh et al. |
| 7,904,178 B2 | 3/2011 | Williams |
| 7,917,213 B2 | 3/2011 | Bulkes |
| 7,933,652 B2 | 4/2011 | Phillips |
| 8,007,440 B2 | 8/2011 | Magnin et al. |
| 8,027,736 B2 | 9/2011 | Wahlstrand |
| 8,036,756 B2 | 10/2011 | Swoyer et al. |
| 8,048,060 B2 | 11/2011 | Griffin et al. |
| 8,055,351 B2 | 11/2011 | Atalar et al. |
| 8,106,657 B2 | 1/2012 | Sakellariou et al. |
| 8,170,691 B2 | 5/2012 | Eckerdal |
| 8,202,259 B2 | 6/2012 | Evans et al. |
| 8,246,643 B2 | 8/2012 | Nita |
| 8,275,464 B2 | 9/2012 | Li et al. |
| 8,280,526 B2 | 10/2012 | Wahlstrand |
| 8,483,842 B2 | 7/2013 | Alexander et al. |
| 8,620,455 B2 | 12/2013 | Alexander et al. |
| 8,676,340 B2 | 3/2014 | Wahlstrand |
| 8,744,598 B2 | 6/2014 | Alexander et al. |
| 8,788,061 B2 | 7/2014 | Mehdizadeth |
| 8,805,534 B2 | 8/2014 | Olsen |
| 8,903,504 B2 | 12/2014 | Hegland |
| 9,002,474 B2 | 4/2015 | Olsen |
| 9,037,263 B2 | 5/2015 | Marshall |
| 9,044,593 B2 | 6/2015 | Li |
| 2001/0044646 A1 | 11/2001 | Marshall et al. |
| 2002/0032468 A1 | 3/2002 | Hill |
| 2002/0038135 A1 | 3/2002 | Connelly et al. |
| 2002/0058978 A1 | 5/2002 | Sass |
| 2002/0183438 A1 | 5/2002 | Amarasekera et al. |
| 2002/0082673 A1 | 6/2002 | Benz et al. |
| 2002/0106918 A1 | 8/2002 | Saito et al. |
| 2002/0111659 A1 | 8/2002 | Davis et al. |
| 2002/0111663 A1 | 8/2002 | Dahl et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |

(56) References Cited

U.S. PATENT DOCUMENTS

| | | |
|---|---|---|
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0143377 A1 | 10/2002 | Wessman et al. |
| 2002/0183740 A1 | 12/2002 | Edwards et al. |
| 2002/0183822 A1 | 12/2002 | Bodner |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0044623 A1 | 3/2003 | Sakurai et al. |
| 2003/0045920 A1 | 3/2003 | Belden et al. |
| 2003/0060732 A1 | 3/2003 | Jacobsen et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0093107 A1 | 5/2003 | Parsonage et al. |
| 2003/0109901 A1 | 6/2003 | Greatbatch |
| 2003/0117787 A1 | 6/2003 | Nakauchi |
| 2003/0120148 A1 | 6/2003 | Pacetti |
| 2003/0120197 A1 | 6/2003 | Kaneko et al. |
| 2003/0135114 A1 | 7/2003 | Pacetti et al. |
| 2003/0139794 A1 | 7/2003 | Jenney et al. |
| 2003/0139806 A1 | 7/2003 | Haverkost et al. |
| 2003/0140931 A1 | 7/2003 | Zeijlemaker |
| 2003/0144704 A1 | 7/2003 | Terry |
| 2003/0144705 A1 | 7/2003 | Funke |
| 2003/0144716 A1 | 7/2003 | Reinke et al. |
| 2003/0144717 A1 | 7/2003 | Hegele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0167052 A1 | 9/2003 | Lee et al. |
| 2003/0204217 A1 | 10/2003 | Greatbatch |
| 2003/0225331 A1 | 12/2003 | Diederich et al. |
| 2004/0020674 A1 | 2/2004 | McFadden et al. |
| 2004/0024442 A1 | 2/2004 | Sowinski et al. |
| 2004/0028859 A1 | 2/2004 | LeGrande et al. |
| 2004/0068307 A1 | 4/2004 | Goble |
| 2004/0071949 A1 | 4/2004 | Glatkowski et al. |
| 2004/0088012 A1 | 5/2004 | Kroll et al. |
| 2004/0106958 A1 | 6/2004 | Mathis et al. |
| 2004/0162600 A1 | 8/2004 | Williams |
| 2004/0167443 A1 | 8/2004 | Shireman et al. |
| 2004/0173368 A1 | 9/2004 | Dickson |
| 2004/0199069 A1 | 10/2004 | Connelly et al. |
| 2004/0220549 A1 | 11/2004 | Dittman et al. |
| 2004/0249428 A1 | 12/2004 | Wang et al. |
| 2004/0251042 A1 | 12/2004 | Weiner et al. |
| 2004/0263172 A1 | 12/2004 | Gray et al. |
| 2004/0263173 A1 | 12/2004 | Gray |
| 2004/0263174 A1 | 12/2004 | Gray et al. |
| 2004/0267328 A1 | 12/2004 | Duffin |
| 2005/0065587 A1 | 3/2005 | Gryzwa |
| 2005/0070972 A1 | 3/2005 | Wahlstrand |
| 2005/0080471 A1 | 4/2005 | Chitre et al. |
| 2005/0113876 A1 | 5/2005 | Weiner |
| 2005/0115624 A1 | 6/2005 | Walak |
| 2005/0137664 A1 | 6/2005 | Sommer et al. |
| 2005/0145307 A1 | 7/2005 | Shireman et al. |
| 2005/0159661 A1 | 7/2005 | Connelly et al. |
| 2005/0182471 A1 | 8/2005 | Wang |
| 2005/0222642 A1 | 10/2005 | Przybyszewski |
| 2005/0222647 A1 | 10/2005 | Wahlstrand |
| 2005/0222656 A1 | 10/2005 | Wahlstrand |
| 2005/0222657 A1 | 10/2005 | Wahlstrand |
| 2005/0222658 A1 | 10/2005 | Hoegh et al. |
| 2005/0222659 A1 | 10/2005 | Olsen |
| 2006/0030918 A1 | 2/2006 | Chinn et al. |
| 2006/0036306 A1 | 2/2006 | Heist et al. |
| 2006/0079926 A1 | 4/2006 | Desai et al. |
| 2006/0089680 A1 | 4/2006 | Bruchmann et al. |
| 2006/0095078 A1 | 5/2006 | Tronnes |
| 2006/0135962 A1 | 6/2006 | Kick et al. |
| 2006/0155270 A1 | 7/2006 | Hancock |
| 2006/0167522 A1 | 7/2006 | Malinowski |
| 2006/0167527 A1 | 7/2006 | Malinowski |
| 2006/0200218 A1 | 9/2006 | Wahlstrand |
| 2006/0224207 A1 | 10/2006 | Dublin |
| 2006/0247747 A1 | 11/2006 | Olsen |
| 2006/0247748 A1 | 11/2006 | Wahlstrand |
| 2007/0021811 A1 | 1/2007 | D'Aquanni et al. |
| 2007/0106332 A1 | 5/2007 | Denker |
| 2007/0123805 A1 | 5/2007 | Shireman et al. |
| 2007/0129779 A1 | 6/2007 | Ayre |
| 2007/0168008 A1 | 7/2007 | Olsen |
| 2007/0185556 A1 | 8/2007 | Williams |
| 2007/0208383 A1 | 9/2007 | Williams |
| 2007/0293924 A1 | 12/2007 | Belden et al. |
| 2008/0033497 A1 | 2/2008 | Bulkes |
| 2008/0039709 A1 | 2/2008 | Karmarkar |
| 2008/0058715 A1 | 3/2008 | Houser et al. |
| 2008/0154326 A1 | 6/2008 | Clyne |
| 2008/0183263 A1 | 7/2008 | Alexander |
| 2008/0195186 A1* | 8/2008 | Li ........................ A61N 1/0551 607/115 |
| 2008/0195187 A1 | 8/2008 | Li |
| 2008/0215008 A1 | 9/2008 | Nance et al. |
| 2008/0242944 A1 | 10/2008 | Sharma |
| 2008/0243081 A1 | 10/2008 | Nance et al. |
| 2008/0243218 A1 | 10/2008 | Bottomley |
| 2008/0262582 A1 | 10/2008 | Alexander |
| 2008/0262584 A1 | 10/2008 | Bottomley |
| 2008/0269863 A1 | 10/2008 | Alexander |
| 2008/0287804 A1 | 11/2008 | Nita |
| 2009/0171421 A1* | 7/2009 | Atalar .................... A61N 1/056 607/63 |
| 2009/0204192 A1 | 8/2009 | Carlton |
| 2009/0221970 A1 | 9/2009 | Spinoza |
| 2009/0228074 A1 | 9/2009 | Edgell et al. |
| 2009/0234402 A1 | 9/2009 | Marshall |
| 2009/0240235 A1 | 9/2009 | Murata |
| 2009/0259272 A1 | 10/2009 | Reddy |
| 2009/0270956 A1* | 10/2009 | Vase ...................... A61N 1/05 607/116 |
| 2009/0287189 A1 | 11/2009 | Suwito |
| 2010/0069743 A1 | 3/2010 | Sheetz et al. |
| 2010/0100164 A1 | 4/2010 | Johnson et al. |
| 2010/0137957 A1 | 6/2010 | Eckerdal |
| 2010/0145426 A1 | 6/2010 | Stone |
| 2010/0198327 A1 | 8/2010 | Helland |
| 2010/0256528 A1 | 10/2010 | Lippert et al. |
| 2010/0256604 A1 | 10/2010 | Lippert et al. |
| 2010/0268310 A1 | 10/2010 | Bonde et al. |
| 2010/0331938 A1 | 12/2010 | Sommer |
| 2011/0015713 A1 | 1/2011 | Min |
| 2011/0034983 A1 | 2/2011 | Min |
| 2011/0071599 A1 | 3/2011 | Olsen |
| 2011/0071604 A1 | 3/2011 | Wahlstrand |
| 2011/0071605 A1 | 3/2011 | Wahlstrand |
| 2011/0112615 A1 | 5/2011 | Hoegh et al. |
| 2011/0230943 A1 | 9/2011 | Johnson et al. |
| 2011/0251487 A1 | 10/2011 | Magnin et al. |
| 2011/0319905 A1 | 12/2011 | Palme et al. |
| 2012/0010689 A1 | 1/2012 | Wahlstrand |
| 2012/0035616 A1 | 2/2012 | Olsen et al. |
| 2012/0035694 A1* | 2/2012 | Olsen ................... A61N 1/3718 607/116 |
| 2012/0035695 A1 | 2/2012 | Olsen et al. |
| 2012/0035696 A1 | 2/2012 | Kern |
| 2012/0035697 A1 | 2/2012 | Stone |
| 2012/0035951 A1 | 2/2012 | Goetz |
| 2012/0041528 A1* | 2/2012 | Mehdizadeh .......... A61N 1/056 607/115 |
| 2012/0041529 A1 | 2/2012 | Olsen |
| 2012/0046722 A1 | 2/2012 | Olsen |
| 2012/0635696 | 2/2012 | Kern |
| 2012/0053664 A1 | 3/2012 | Hegland |
| 2012/0059467 A1 | 3/2012 | Drew |
| 2012/0130461 A1 | 5/2012 | Olsen |

(56) References Cited

U.S. PATENT DOCUMENTS

| | | |
|---|---|---|
| 2012/0330383 A1 | 12/2012 | Wahlstrand |
| 2013/0282088 A1 | 10/2013 | Bondhus |
| 2013/0296991 A1 | 11/2013 | Alexander et al. |
| 2014/0107746 A1 | 4/2014 | Alexander et al. |
| 2014/0200643 A1 | 7/2014 | Wahlstrand |
| 2014/0288626 A1 | 9/2014 | Alexander et al. |
| 2014/0345132 A1 | 11/2014 | Mehdizadeh et al. |
| 2014/0350654 A1 | 11/2014 | Olsen et al. |
| 2015/0082618 A1 | 3/2015 | Hegland |
| 2015/0170792 A1 | 6/2015 | Alford |
| 2015/0374977 A1 | 12/2015 | Howard et al. |

FOREIGN PATENT DOCUMENTS

| | | |
|---|---|---|
| EP | 0713714 | 5/1996 |
| EP | 0760196 | 3/1997 |
| EP | 0920239 | 6/1999 |
| EP | 1273922 | 1/2003 |
| EP | 1424095 | 6/2004 |
| EP | 1466576 | 10/2004 |
| EP | 1625875 | 2/2006 |
| EP | 1632265 | 3/2006 |
| EP | 1935449 | 6/2008 |
| GB | 2429154 | 2/2007 |
| JP | 07/255863 | 10/1995 |
| JP | 11/086641 | 3/1999 |
| WO | WO95/032673 | 12/1995 |
| WO | WO96/016694 | 6/1996 |
| WO | WO96/028951 | 9/1996 |
| WO | WO97/041923 | 11/1997 |
| WO | WO98/048896 | 11/1998 |
| WO | WO99/010035 | 3/1999 |
| WO | WO99/019020 | 4/1999 |
| WO | WO99/060370 | 11/1999 |
| WO | WO00/027279 | 5/2000 |
| WO | WO01/080940 | 11/2001 |
| WO | WO02/000292 | 1/2002 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO04/012809 | 2/2004 |
| WO | WO04/052448 | 6/2004 |
| WO | WO04/073040 | 8/2004 |
| WO | WO05/030322 | 4/2005 |
| WO | WO05/032654 | 4/2005 |
| WO | WO05/102444 | 11/2005 |
| WO | WO05/102445 | 11/2005 |
| WO | WO05/102446 | 11/2005 |
| WO | WO05/102447 | 11/2005 |
| WO | WO06/031317 | 3/2006 |
| WO | WO06/093685 | 9/2006 |
| WO | WO06/093686 | 9/2006 |
| WO | WO06/118640 | 11/2006 |
| WO | WO06/118641 | 11/2006 |
| WO | WO07/047966 | 4/2007 |
| WO | WO07/124273 | 11/2007 |
| WO | WO07/126657 | 11/2007 |
| WO | WO07/149757 | 12/2007 |
| WO | WO08/088568 | 7/2008 |
| WO | WO08/100839 | 8/2008 |
| WO | WO08/100840 | 8/2008 |
| WO | WO08/111986 | 9/2008 |
| WO | WO08/130409 | 10/2008 |
| WO | WO08/134196 | 11/2008 |
| WO | WO08/140376 | 11/2008 |
| WO | WO09/011440 | 9/2009 |
| WO | WO09/134901 | 11/2009 |
| WO | WO10/062988 | 6/2010 |
| WO | WO10/126871 | 11/2010 |
| WO | WO10/126877 | 11/2010 |
| WO | WO10/126884 | 11/2010 |
| WO | WO10/126887 | 11/2010 |
| WO | WO10/126935 | 11/2010 |
| WO | WO10/126939 | 11/2010 |
| WO | WO10/126943 | 11/2010 |
| WO | WO10/126946 | 11/2010 |
| WO | WO10/126949 | 11/2010 |
| WO | WO10/126975 | 11/2010 |
| WO | WO10/135440 | 11/2010 |
| WO | WO11/019416 | 2/2011 |
| WO | WO12/103419 | 8/2012 |
| WO | WO13/158189 | 10/2013 |

OTHER PUBLICATIONS

PCT/US2004/042081: Search Report and Written Opinion.
PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Baker et al., "Evaluation of Specific Absorption Rates as a Dosimeter of MRI-Related Implant Heating", Journal of Magnetic Resonance Imaging 20:315-320 (2004).
Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.
Chung, D.D.L., "Carbon Fiber Composites", 1994, chapter 1, p. 8, table 1.2, Elsevier, ISBN: 978-0-7506-9169-7.
Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.
Chung, D.D.L., Electromagnetic Interference Shielding Effectiveness of Carbon Materials, Carbon 29 (2001) pp. 279-285, Elsevier Science Ltd.
Engdahl, Tomi, "Ground Loop Basics." Web Jan. 4, 2009, ePanorama. net www.epanorama.net/documents/groundloop/basics.html 28052. 00 U.S. Appl. No. 11/739,787.
Finelli, D., et al., "MRI Imaging-Related Heating of Deep Brain Stimulation Electrodes: In Vitro Study", AJNR Am. J. Neuroadiol 23:1, Nov./Dec. 2002.
Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_qu3776/is_200403/ai_n9405_582/print.
Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.
Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.
Kolin, et al., "Miniaturization of the Electromagnetic Blood Flow Meter and Its Use for the Recording of Circulatory Responses of

(56) References Cited

OTHER PUBLICATIONS

Conscious Animals to Sensory Stimuli", Department of Biophysics, University of California at Los Angeles, Aug. 1959, Proc. N.A.S. vol. 45(8), pp. 1312-1321.
Medtronic Activa Product Family and Procedure Solution Brochure, Medtronic, Inc, 2001.
Medtronic Neurostimulation Systems Brochure, Medtronic, Inc., 2002.
Oscor, Inc. Product Catalog, 2008 28052.00.
Quick et al., "Endourethral MRI", Magnetic Resonance in Medicine, 45:138-146, 2001.
Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.
Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.
U.S. Appl. No. 14/807,323, filed Jul. 23, 2015.
U.S. Appl. No. 14/807,323 Restriction Requirement, dated Apr. 26, 2016.
U.S. Appl. No. 14/807,323, Response Filed Jun. 20, 2016.
U.S. Appl. No. 14/807,323, Non-Final Office Action, dated Jul. 13, 2016.
U.S. Appl. No. 14/807,323, Response Filed Oct. 13, 2016.
U.S. Appl. No. 14/807,323, Final Office Action, dated Feb. 1, 2017.
U.S. Appl. No. 14/807,323, Response Filed Apr. 21, 2017.
U.S. Appl. No. 14/807,323, Advisory Action, dated May 1, 2017.
U.S. Appl. No. 14/807,323, RCE Request and Response filed May 31, 2017.
U.S. Appl. No. 14/807,323 Non-Final Office Action, dated Jun. 27, 2017.
U.S. Appl. No. 14/807,323, Response Filed Sep. 27, 2017.

\* cited by examiner

METHODS OF SHIELDING IMPLANTABLE
MEDICAL LEADS AND IMPLANTABLE
MEDICAL LEAD EXTENSIONS

TECHNICAL FIELD

Embodiments relate to implantable medical leads and implantable medical lead extensions. More particularly, embodiments relate to methods of shielding implantable medical leads and implantable medical lead extensions.

BACKGROUND

Implantable medical systems are used to provide stimulation therapy and/or physiological sensing for patients. The implantable medical system includes a stimulation or sensing device that is implanted at a convenient location. Implantable medical leads are routed between the site of implantation of the device and a target site where stimulation or sensing is to occur. Where the route is lengthy, an implantable medical lead extension is used to traverse a portion of that distance.

The implantable medical leads include one or more electrical contacts located near a proximal end of the lead. Where no extension is needed, the proximal end of the lead is physically connected to the stimulation or sensing device so that the proximal contacts of the lead are electrically coupled to electrical circuitry of the device. For scenarios where the implantable medical lead extension is used, then the proximal end of the lead is physically connected to a distal end of the extension where electrical connectors of the extension are coupled to the electrical contacts of the lead. The proximal end of the extension is physically connected to the stimulation or sensing device so that the proximal contacts of the extension are electrically coupled to electrical circuitry of the device. The leads also include one or more electrodes located near a distal end of the leads. Electrical conductors are present within the lead, and each electrical conductor is connected to a respective electrical contact and electrode to provide an electrical path for stimulation and/or sensed signals. Electrical conductors are also present within the extension, and each electrical conductor is connected to a respective electrical contact and distal connector to provide an electrical path for stimulation and/or sensed signals.

Because the lead and lead-extension combination extends over a significant distance within the body, each electrical conductor within the lead and extension is susceptible to receiving extraneous electromagnetic energy that produces electrical current on the electrical conductor. While most ambient conditions expose the lead and lead extension to insignificant levels of such extraneous electromagnetic energy, certain situations may create levels of extraneous electromagnetic energy that are of concern. An example of such a situation is a magnetic resonance imaging (MRI) scan. The MRI scan utilizes a high energy radio frequency (RF) electromagnetic signal. This RF signal may produce relatively large levels of electrical current on the electrical conductor of the lead and extension when the patient having the implantable medical system that includes the lead and/or lead extension combination undergoes the MRI scan. The relatively large electrical current that results from the high energy RF signal produces heating at the electrodes that may create discomfort and even dangerous tissue damage at the site within the body where the one or more electrodes of the lead are located.

It has been found that a shield layer within the lead reduces the amount of RF energy that reaches the electrical conductors, which in turn reduces the amount of current being coupled onto the electrical conductors and reduces the heating at the electrodes to acceptable levels. The manufacturing process of the lead has been altered to include a shield layer when the lead body is being manufactured by creating an inner jacket over the electrical conductor, then creating the shield layer on the inner jacket, and then creating an outer jacket over the inner jacket. The electrical contacts and electrodes are then installed about the inner jacket and are coupled to the electrical conductor to complete the leads. However, leads and extensions that have been constructed without such shield layers or other protective aspects remain vulnerable to the high levels of RF energy of the MRI scan or other situation.

SUMMARY

Embodiments address issues such as these and others by adding a shield layer onto the exterior surface of an insulative lead body of an existing lead having electrical contacts and electrodes already installed on that lead body. The shield layer is then covered by an insulative layer.

Embodiments provide a method of shielding an implantable medical lead. The method involves providing a shield layer onto an exterior surface of an insulative lead body of the implantable medical lead between an electrical contact on a proximal end of the insulative lead body and an electrode on a distal end of the insulative lead body with a proximal end of the shield layer being spaced distally from the electrical contact and with a distal end of the shield layer being spaced proximally from the electrode. The method further involves applying an outer insulative layer onto the shield layer while the shield layer is present on the exterior surface of the insulative layer with the outer insulative layer being located between the electrical contact and the electrode.

Embodiments provide a method of shielding an implantable medical lead. The method involves utilizing the implantable medical lead as a mandrel for a braiding machine to braid wires onto an insulative lead body of the implantable medical lead between an electrical contact on a proximal end of the implantable medical lead and an electrode on a distal end of the implantable medical lead with a proximal end of the shield layer being spaced distally from the electrical contact and with a distal end of the shield layer being spaced proximally from the electrode. The method further involves applying an outer insulative layer onto the braided wires while the braided wires are present on the insulative lead body of the implantable medical lead with the outer insulative layer being located between the electrical contact and the electrode.

Embodiments provide a method of shielding an implantable medical lead extension. The method involves providing a shield layer onto an exterior surface of an insulative lead body of the implantable medical lead extension between an electrical contact on a proximal end of the implantable medical lead extension and a distal end of the implantable medical lead extension with a proximal end of the shield layer being spaced distally from the electrical contact. The method further involves applying an outer insulative layer onto the shield layer with the outer insulative layer being located between the electrical contact and the distal end.

Embodiments provide a method of shielding an implantable medical lead extension. The method involves utilizing the implantable medical lead extension as a mandrel for a braiding machine to braid wires onto an insulative lead body of the implantable medical lead extension between an electrical contact on a proximal end of the implantable medical lead extension and a distal end of the implantable medical lead extension with a proximal end of the shield layer being spaced distally from the electrical contact. The method further involves applying an outer insulative layer onto the braided wires on the implantable medical lead extension with the outer insulative layer being located between the electrical contact and the distal end.

Embodiments provide an implantable medical lead that includes a lead body defining a lumen, a conductor within the lumen, a proximal contact coupled to a proximal area of the lead body, and a distal electrode coupled to a distal area of the lead body, with the conductor electrically coupling the proximal contact to the distal electrode. The implantable medical lead further includes an inner insulative layer coupled to the outer surface of the lead body, a shield layer positioned about the inner insulative layer and between the proximal contact and the distal electrode, and an outer insulative layer positioned about the shield layer and between the proximal contact and the distal electrode.

Embodiments provide an implantable medical lead extension that includes a lead body defining a lumen, a conductor within the lumen, a proximal contact coupled to a proximal area of the lead body, and a distal connector housing coupled to a distal area of the lead body with a distal connector positioned within the distal connector housing, the conductor electrically coupling the proximal contact to the distal connector. The implantable medical lead extension further includes an inner insulative layer coupled to the outer surface of the lead body, a shield layer positioned about the inner insulative layer and between the proximal contact and the distal connector housing, and an outer insulative layer positioned about the shield layer and between the proximal contact and the distal connector housing.

DETAILED DESCRIPTION

Embodiments provide a shield layer for an existing implantable lead and/or implantable lead extension. This provides a method of manufacturing a lead or extension with a shield layer where a conventional manufacturing technique may be used to create a complete lead or lead extension and then the shield layer is added as a subsequent process. This further provides the ability to retrofit the shield layer to leads and lead extensions that have already been constructed and are present in available inventory so that this existing inventory is made safer for MRI scans.

Figure 1:
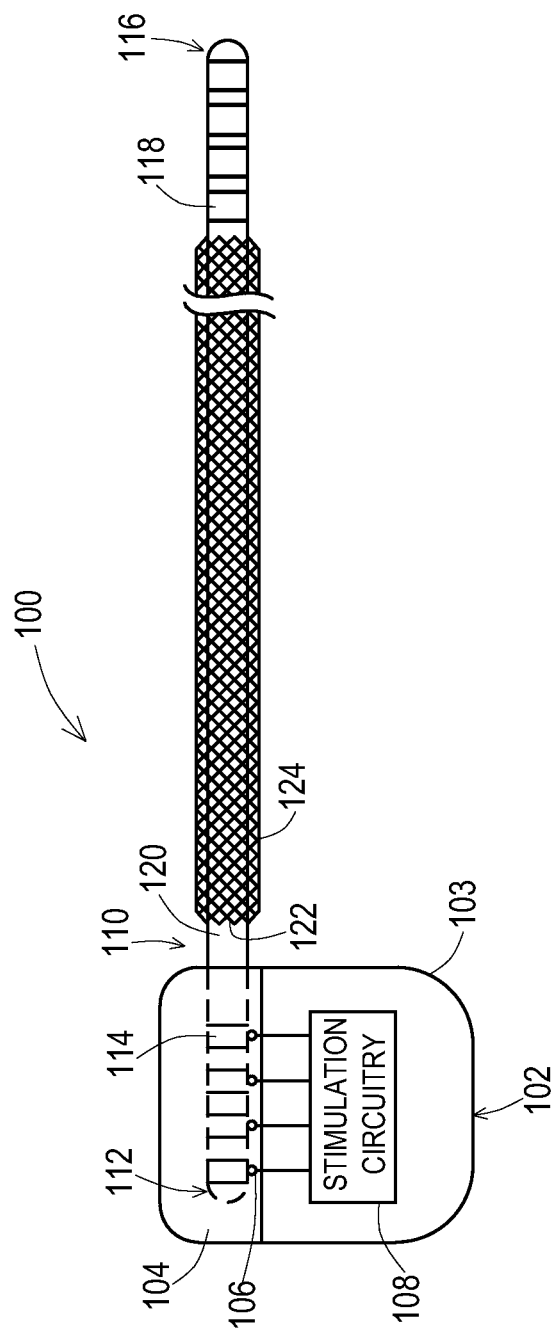
FIG. 1 shows an example of an implantable medical system that includes a lead having an added shield layer according to various embodiments.

FIG. 1 shows one example of an implantable medical system 100 that includes an implantable medical device 102 coupled to an implantable medical lead 110. A proximal end 112 of the lead 110 is present within a connection block 104 of the medical device 102 where electrical contacts 114 of the lead 110 are electrically connected to connectors 106 of the connection block 104. The connectors 106 are electrically coupled to stimulation and/or sensing circuitry 108 within a housing 103 of the medical device 102. A distal end 116 of the lead is routed to the stimulation site where electrodes 118 on the distal end 116 provide the stimulation signals to the tissue and/or sense signals from the tissue. Electrical conductors are present inside the lead 110 to electrically connect the contacts 114 with the electrodes 118.

According to the embodiment shown, the lead 110 has an added shield layer 122 that has been applied to an existing outer layer 120 of the lead body of the lead 110. This shield layer 122 may be of various forms such as a tubular structure of braided conductive wires that have been overbraided atop the existing outer insulative layer 120, a tubular conductive foil structure, and the like. For a braided shield, the wires of the braid may be a conductor such as a biocompatible metal like tantalum, titanium, and the like. For a foil shield, the foil may be a conductor such as biocompatible metal like tantalum, titanium, and the like.

Where the shield layer 122 is a braided wire shield as shown in FIG. 1, the braid may be created with a variety of shield parameters. Examples of shield parameters such as braid angle, wire cross-sectional shape and diameter, number of braid wires, braid depth, distance from shield termination to closest contact or electrode, and the like that may also be used for the embodiments being disclosed herein are described in U.S. patent application Ser. No. 13/264,067, which is incorporated herein by reference in its entirety.

As can be seen, the added shield layer 122 is present with a proximal end of the shield layer 122 starting distally of a most distal proximal contact 114 and ending proximally of a most proximal distal electrode 118. Likewise, an outer insulative layer 124 is applied atop the shield layer 122 with a proximal end of the outer insulative layer 124 starting distally of the most distal proximal contact 114 and ending proximally of the most proximal distal electrode 118 to thereby entirely cover the added shield layer 122. This prevents exposure of the added shield layer 122 to the tissue surround the lead 110.

While the shield layer 122 is not in direct contact with the tissue along the length of the lead 110, high frequency RF energy coupled onto the shield layer 122, such as during an MRI scan, may capacitively couple to the surrounding tissue to dissipate the RF energy over the length of the shield layer 122. Thus, there is a significant amount of tissue where the RF energy is being dissipated, rather than a small amount of tissue where the electrodes 118 are located. Furthermore, if desired, ground rings could be added atop the shield layer 122 where the ground rings are exposed to provide a direct path for current from the shield layer 122 to the tissue or from the shield layer 122 to a ground connection at the device 102.

Thus, the lead 110 may be manufactured in a conventional manner and then the shield layer 122 and insulative layer 124 may be added as subsequent steps. Furthermore, the lead 110 may exist in inventory and may be retrieved from inventory for a retrofit of the shield layer 122 and insulative layer 124.

Figure 2:
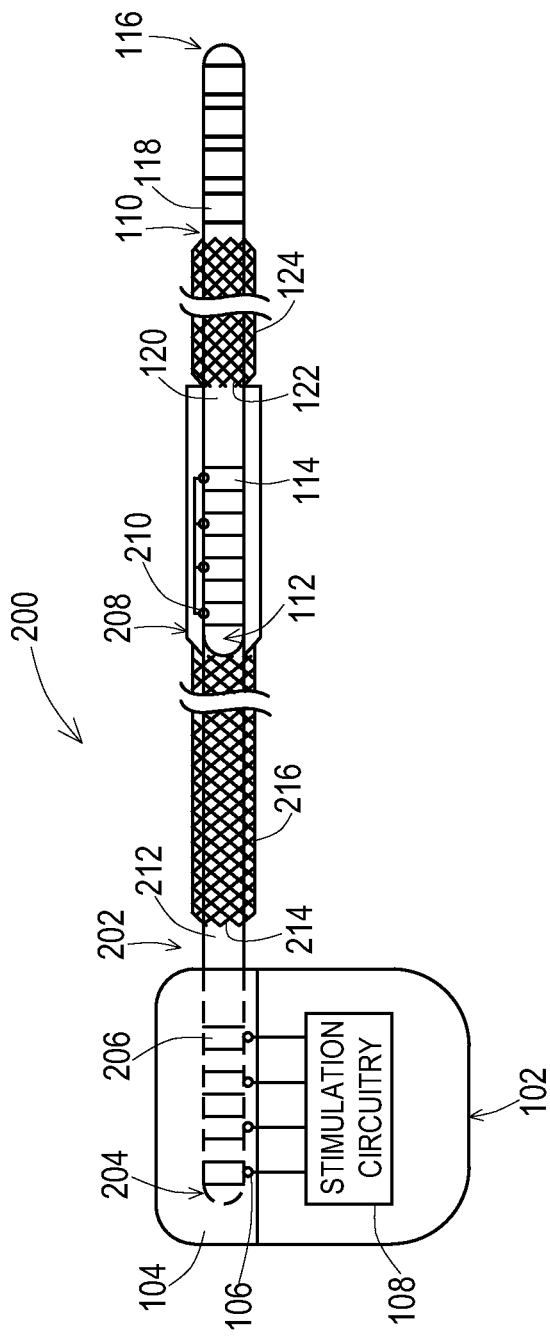
FIG. 2 shows an example of an implantable medical system that includes a lead extension having an added shield layer according to various embodiments.

FIG. 2 shows one example of an implantable medical system 200 that includes the implantable medical device 102 coupled to an implantable medical lead extension 202 that is in turn coupled to the implantable medical lead 110. A proximal end 112 of the lead 110 is present within a distal connection block 208 of the extension 202 where electrical contacts 114 of the lead 110 are electrically connected to connectors 210 of the connection block 208 of the extension. A proximal end 204 of the extension 202 is coupled to the connection block 104 of the medical device 102 where electrical contacts 206 of the extension are electrically connected to connectors 106 of the connection block 104. The distal end 116 of the lead is routed to the stimulation site where the electrodes 118 on the distal end 116 provide the stimulation signals to the tissue and/or sense signals from the tissue. Electrical conductors are present inside the lead 110 to electrically connect the contacts 114 with the electrodes 118 and electrical conductors are present inside the extension 202 to electrically connect the connectors 210 to the contacts 206.

According to the embodiment shown, the extension 202 has an added shield layer 214 that has been applied to an existing outer layer 212 of the lead body of the extension 202. As with the shield layer 122 of the lead 110 in FIG. 1, this shield layer 214 of the extension 202 may be of various forms such as a tubular structure of braided conductive wires that have been overbraided atop the existing outer insulative layer 120, a tubular conductive foil structure, and the like. Where the shield layer 214 is a braided wire shield as shown in FIG. 2, the braid may be created with a variety of shield parameters as described above for the shield layer 122 and as described in U.S. patent application Ser. No. 13/264,067.

As can be seen, the added shield layer 202 is present with a proximal end of the shield layer 214 starting distally of a most distal proximal contact 206 and ending proximally of a most proximal distal connector 210 within the connector block 208. Likewise, an outer insulative layer 216 is applied atop the shield layer 214 with a proximal end of the outer insulative layer 216 starting distally of the most distal proximal contact 206 and ending proximally of the most proximal distal connector 210 to thereby entirely cover the added shield layer 214. This prevents exposure of the added shield layer 214 to the tissue surrounding the extension 202.

While the shield layer 214 is not in direct contact with the tissue along the length of the extension 202, high frequency RF energy coupled onto the shield layer 214, such as during an MRI scan, may capacitively couple to the surrounding tissue to dissipate the RF energy over the length of the shield layer 214. Thus, there is a significant amount of tissue where the RF energy is being dissipated for the extension, rather than a small amount of tissue where the electrodes 118 of the lead 110 are located. Furthermore, if desired, ground rings could be added atop the shield layer 214 where the ground rings are exposed to provide a direct path for current from the shield layer 214 to the tissue or from the shield layer 214 to a ground connection at the device 102.

Thus, the extension 202 may also be manufactured in a conventional manner and then the shield layer 214 and insulative layer 216 may be added as subsequent steps. Furthermore, the extension 202 may exist in inventory and may be retrieved from inventory for a retrofit of the shield layer 214 and insulative layer 216.

As shown in FIG. 2, the lead 110 attached to the extension 202 also includes the added shield layer 122. However, the extension 202 having the shield layer 214 may be used in conjunction with other leads such as leads that have integral shields or even leads that have no shield where the risk of RF coupling to the lead is not as problematic. Similarly, the lead 110 having the added shield layer 122 may be used in conjunction with other extensions including extensions that have integral shields rather than shields that have been added.

Figure 3:
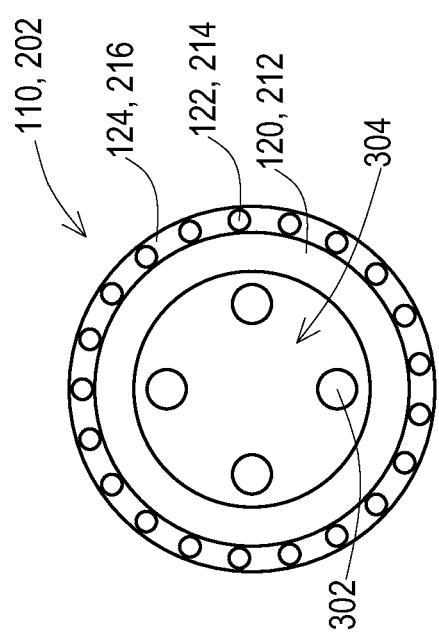
FIG. 3 shows a lateral cross-sectional view of a lead or lead extension having an added shield layer according to various embodiments.

FIG. 3 shows a cross-section of a lead 110 or lead extension 202. The original construction of the lead 110 or lead extension 202 includes the lead body 120, 212. Electrical conductors 302 are present within the lead body 120, 212. The lead body 120, 221 may define a lumen 304 that the conductors 302 pass through when extending from the proximal end to the distal end. The electrical conductors 302 are electrically coupled to the proximal contacts and the distal electrode of the lead or distal connector of the lead extension.

The shield layer 122, 214 is then added about the lead body 120, 212. The shield layer 122, 214 may be added by sliding a loose fitting shield layer, such as the tubular braid of wires or a tubular foil on the lead body 120, 212. Alternatively, the shield layer may be extruded or braided directly onto the lead body 120, 212. This alternative is discussed in more detail below with reference to FIG. 5.

The outer insulative layer 124, 216 is then added over the shield layer 122, 214. The outer insulative layer 124 may be extruded onto the shield layer 122, 214 or may be a tubular structure such as a polyurethane heat shrink tube that fits loosely over the shield layer 122, 214. Once heated the heat shrink tube then shrinks to tightly fit against the shield layer 122, 214 and the lead body 120, 212 which fixes the position of the shield layer 122, 214 and also provides separation of the shield layer 122, 214 from the exterior conditions.

Figure 4:
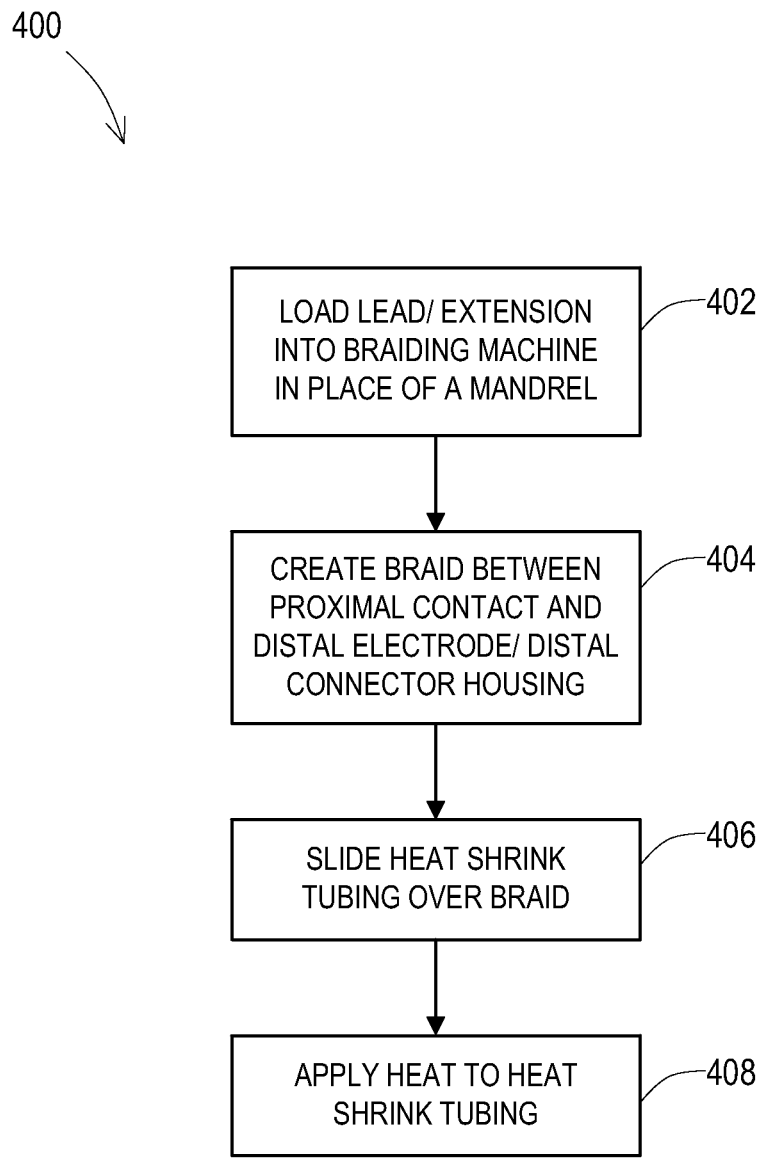
FIG. 4 shows an example of a logical flow of operations to add the shield layer to an existing lead or extension.

One example of operations 400 for constructing the lead or lead extension with the added shield layer is shown in FIG. 4. In this example, the shield layer is a braided tubular structure that is created by braiding the wires directly onto the lead body. At an operation 402, the lead body of the lead or lead extension is loaded into a braiding machine that ordinarily braids wires onto a mandrel. However, the lead body acts as the mandrel. The braid is then created onto the lead body between the proximal contact and the distal electrode or distal connector housing at an operation 404. In this example, a heat shrink tubing is used to provide the outer insulative layer. This heat shrink tubing is positioned by sliding the tubing over the braided shield layer now present on the lead body at an operation 406. Heat is then applied to the heat shrink tubing to cause it to shrink against the braided shield layer at an operation 408.

Figure 5:
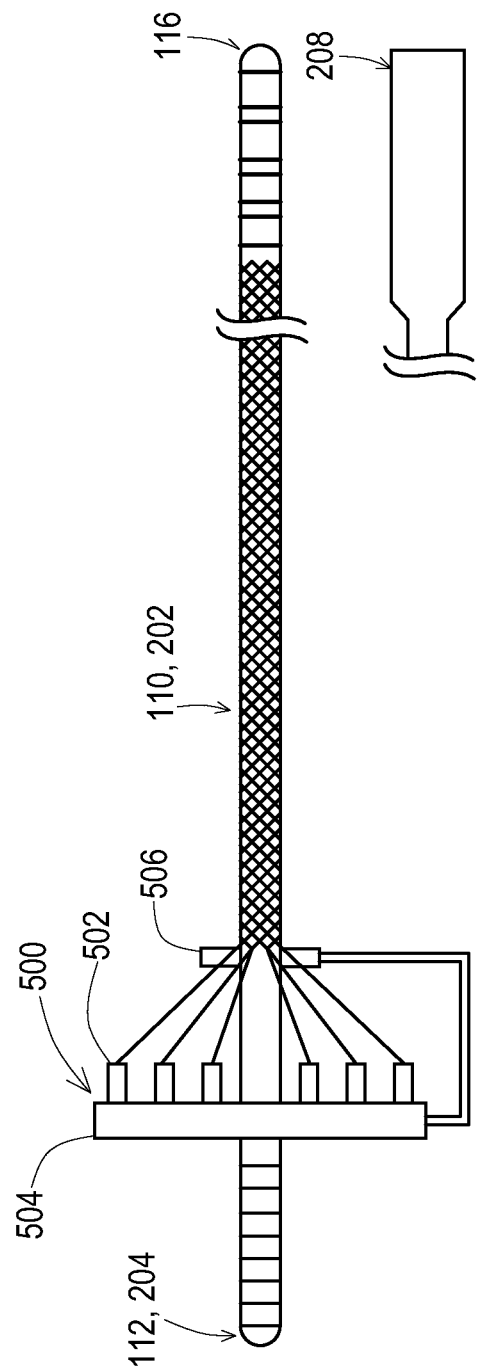
FIG. 5 shows an example of a braiding machine configuration for adding a braided shield layer to an existing lead.

An example of the braiding machine configuration that may be used to complete the operations 402 and 404 of FIG. 4 is shown in FIG. 5. The conventional braiding machine 500 includes a spool support 504, individual spools of wire 502, and a braiding mechanism 506 that guides the wires into the braided configuration onto a mandrel. However, in this configuration, the lead 110 or lead extension 202 is fed through the braiding mechanism 506 in place of a mandrel. As the lead 110 or lead extension 202 moves to the right as shown, the wires are braided onto the lead body.

Figure 6:
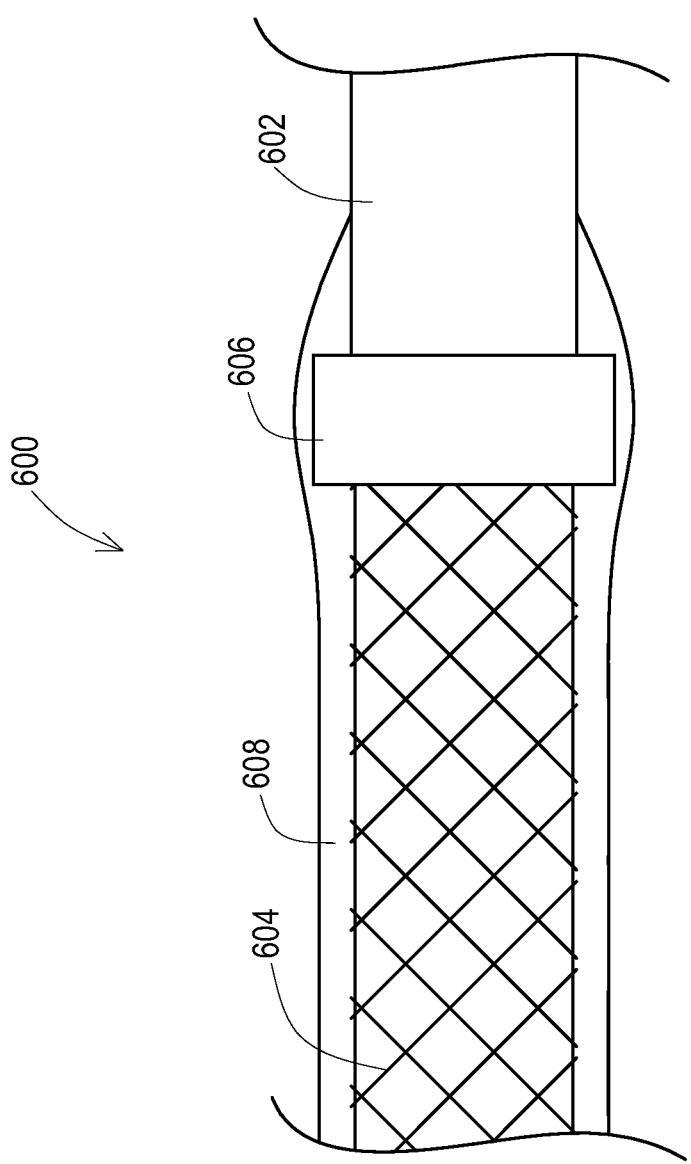
FIG. 6 shows an example of a lead or lead extension having an added shield layer with a shield terminator.

FIG. 6 shows another embodiment of a lead or lead extension 600 that has a shield layer 604 that has been added to the lead body 602. Prior to application of the outer insulative layer 608, a shield terminator 606 is positioned over the end of the shield layer 604. The shield terminator 606 may be of various forms. For instance, the shield terminator 606 may be a ring that is crimped onto the end of the shield layer 604. This is particularly beneficial for a braided wire shield layer as the ring terminator 606 contains the braid wires and prevents the braid wires from migrating radially through the insulative layer 608. As another example, the terminator 606 may be a polyurethane heat shrink terminator that covers only the end portion of the shield layer 604 and is heated to contain the end of the shield layer 604.

As shown, the insulative layer 608 is applied over the shield layer 604 and may also be applied over the shield terminator 606. Where the terminator 606 is a heat shrink terminator, the result is a heat shrink terminator then covered by an outer insulative layer 608 that may also be a heat shrink tubing.

Alternatively, where the terminator is a biocompatible conductive material such as a biocompatible metal ring, the insulative layer 608 may be stopped prior to covering the shield terminator 606 which allows the shield terminator 606 be exposed to the external conditions. This allows the terminator 606 to provide a ground path from the shield layer to a ground connector of the implantable device 102 that electrically couples to the terminator 606 or a ground path directly to tissue in contact with the terminator 606.

Figure 7:
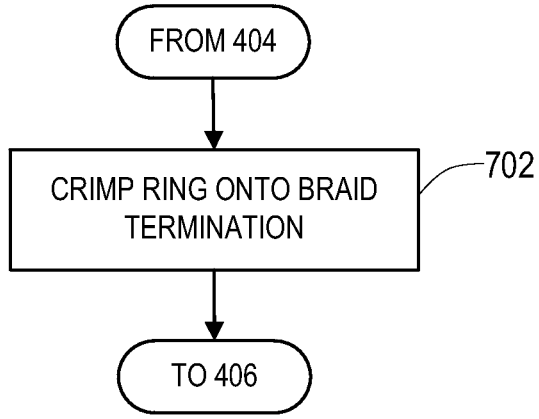
FIG. 7 shows another example of a logical flow of operations to add the shield layer with a crimped shield terminator to an existing lead or extension.

FIG. 7 shows an alteration to the operations 400 of FIG. 4 in order to provide the metal ring terminator. Immediately after operation 404 and prior to operation 406 of FIG. 4, the metal ring is placed over the end of the shield layer and is then crimped tightly against the shield layer at an operation 702. The outer insulative layer may then be positioned over the shield layer at the operation 406 as described above in relation to FIG. 4.

Figure 8:
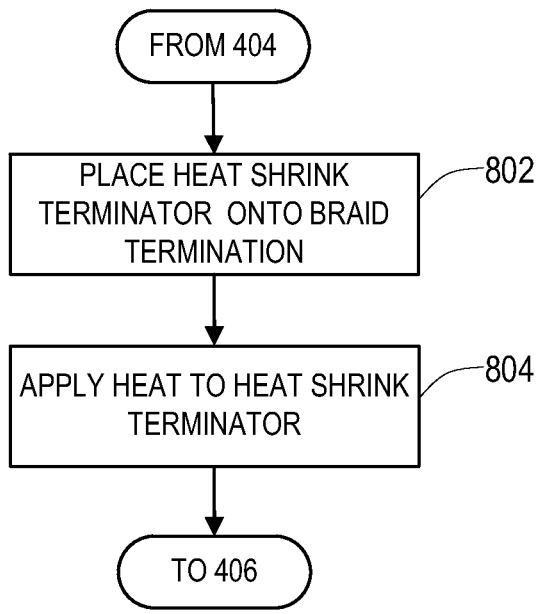
FIG. 8 shows another example of a logical flow of operations to add the shield layer with an additional insulative shield terminator to an existing lead or lead extension.

FIG. 8 shows an alteration to the operations 400 of FIG. 4 in order to provide the heat shrink terminator. Immediately after operation 404 and prior to operation 406 of FIG. 4, the heat shrink terminator is placed over the end of the shield layer at an operation 802. Heat is then applied to the heat shrink terminator at an operation 804 to cause the heat shrink terminator to tighten against the end of the shield layer. The outer insulative layer may then be positioned over the shield layer at the operation 406 as described above in relation to FIG. 4.

Figure 9:
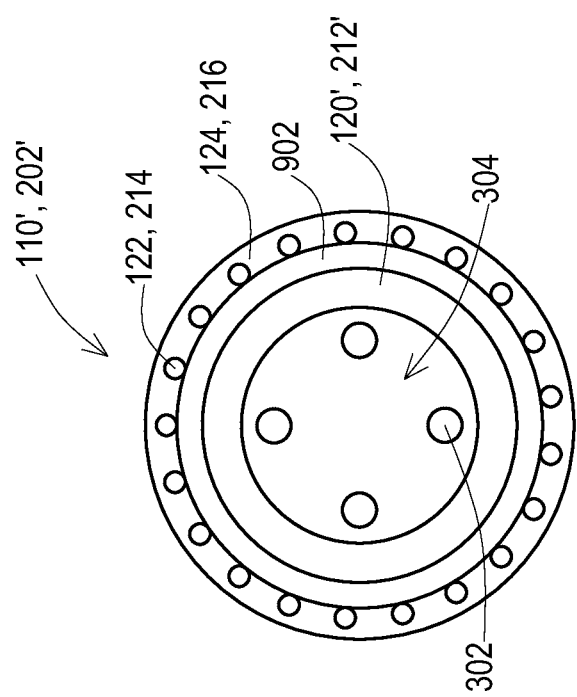
FIG. 9 shows a lateral cross-sectional view of a lead or lead extension having an added shield layer and an added inner insulative layer according to various embodiments.

FIG. 9 shows a cross-section of an alternative embodiment that adds an inner insulative layer onto the lead body of a lead 110' or lead extension 202' prior to adding the shield layer. This embodiment may be useful where the lead body of the existing lead 110' or lead extension 202' is a material that may not be appropriate for receiving the shield layer directly due to being too soft or lacking bonding strength to the metal of the shield layer and/or polymers of the outer insulative layer. For instance, the lead body 120', 212' may be a silicone material to provide a very high degree of flexibility. However, it may be appropriate to shield a portion of the lead body 120', 212' where the high degree of flexibility is not needed. For example, a lead being used for deep brain stimulation may need to be very flexible at the entry point to the brain where a sharp bend of the lead body is necessary. Yet it may be acceptable for that lead to be stiffer in the area where the lead passes by the ear. Therefore, in that section that may be stiffer, the inner insulative layer 902 may be added to the lead body 120', 212' where that inner insulative layer 902 may be a material such as a polyurethane heat shrink tubing.

The shield layer 122, 214 is applied onto the inner insulative layer 902 as in the prior embodiments. The inner insulative layer 902 protects the lead body 120', 212' which may be more vulnerable to damage from the shield layer 122, 214 due to being a very soft and flexible material. The outer insulative layer 124, 216 is then applied over the shield layer 122, 214 as discussed above for the prior embodiments.

Figure 10:
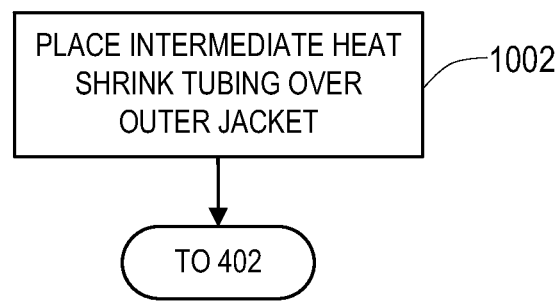
FIG. 10 shows another example of a logical flow of operations to add the shield layer and an inner insulative layer to an existing lead or extension.

FIG. 10 shows an alteration to the operations 400 of FIG. 4 in order to provide the inner insulative layer. Immediately before the operation 402 of FIG. 4, the heat shrink tubing which acts as the inner insulative layer 902 in this example is placed over the lead body 120', 212' at an operation 1002. Heat may be applied to the heat shrink tubing at this point or alternatively may be heated when heating the outer insulative layer. The lead 110' or lead extension 202' may then be positioned into the braiding machine at the operation 402 as described above in relation to FIG. 4 or may otherwise receive the shield layer 122, 214 and the operations of FIG. 4 proceed. The resulting lead or extension maintains flexibility where needed while being shielded in other areas.

While embodiments have been particularly shown and described, it will be understood by those skilled in the art that various other changes in the form and details may be made therein without departing from the spirit and scope of the invention.

What is claimed is:

1. An implantable medical lead, comprising:
   an insulative linear lead body defining a lumen;
   a conductor within the lumen;
   a proximal contact coupled to a proximal area of the lead body and in direct contact with the proximal area of the lead body;
   a distal electrode coupled to a distal area of the lead body, with the conductor electrically coupling the proximal contact to the distal electrode;
   an inner insulative layer coupled to and in direct contact with the outer surface of the linear lead body over the complete circumference of the outer surface of the lead body;
   a shield layer positioned about and in direct contact with the inner insulative layer and between the proximal contact and the distal electrode; and
   an outermost insulative layer positioned about and in direct contact with the shield layer and between the proximal contact and the distal electrode.

2. The implantable medical lead of claim 1, wherein the shield layer comprises braided wires on the outer surface of the inner insulative layer.

3. The implantable medical lead of claim 1, wherein the shield layer comprises tantalum.

4. The implantable medical lead of claim 1, wherein the outermost insulative layer comprises a polymer heat shrink tubing.

5. The implantable medical lead of claim 1, further comprising a terminator positioned on an end of the shield layer.

6. The implantable medical lead of claim 1, wherein the distal electrode is in direct contact with the distal area of the lead body.

7. The implantable medical lead of claim 1, wherein the outer insulative layer has a diameter and wherein the diameter of the outer insulative layer exceeds a diameter of the proximal contact.

8. The implantable medical lead of claim 1, wherein the outer insulative layer has a diameter and wherein the diameter of the outer insulative layer exceeds a diameter of the distal electrode.

9. The implantable medical lead of claim 1, wherein the shield layer has a diameter and wherein the diameter of the shield layer exceeds a diameter of the proximal contact.

10. The implantable medical lead of claim 1, wherein the shield layer has a diameter and wherein the diameter of the shield layer exceeds a diameter of the distal electrode.

11. An implantable medical lead, comprising:
an insulative linear lead body defining a lumen;
a conductor within the lumen;
a proximal contact coupled to a proximal area of the lead body;
a distal electrode coupled to a distal area of the lead body and in direct contact with the distal area of the lead body, with the conductor electrically coupling the proximal contact to the distal electrode;
an inner insulative layer coupled to and in direct contact with the outer surface of the linear lead body over the complete circumference of the outer surface of the lead body;
a shield layer positioned about and in direct contact with the inner insulative layer and between the proximal contact and the distal electrode; and
an outermost insulative layer positioned about and in direct contact with the shield layer and between the proximal contact and the distal electrode.

12. The implantable medical lead of claim 11, wherein the proximal contact is in direct contact with the proximal area of the lead body.

13. The implantable medical lead of claim 11, wherein the outer insulative layer has a diameter and wherein the diameter of the outer insulative layer exceeds a diameter of the proximal contact.

14. The implantable medical lead of claim 11, wherein the outer insulative layer has a diameter and wherein the diameter of the outer insulative layer exceeds a diameter of the distal electrode.

15. The implantable medical lead of claim 11, wherein the shield layer has a diameter and wherein the diameter of the shield layer exceeds a diameter of the proximal contact.

16. The implantable medical lead of claim 11, wherein the shield layer has a diameter and wherein the diameter of the shield layer exceeds a diameter of the distal electrode.

* * * * *